(12) United States Patent
Santilli

(10) Patent No.: US 6,361,492 B1
(45) Date of Patent: Mar. 26, 2002

(54) SURGICAL STABILIZER

(75) Inventor: Albert N. Santilli, Pepper Pike, OH (US)

(73) Assignee: Kapp Surgical Instrument, Inc., Cleveland, OH (US)

(*) Notice: Subject to any disclaimer, the term of this patent is extended or adjusted under 35 U.S.C. 154(b) by 0 days.

(21) Appl. No.: 09/420,164

(22) Filed: Oct. 18, 1999

Related U.S. Application Data

(63) Continuation of application No. 09/049,597, filed on Mar. 27, 1998, now Pat. No. 5,967,972
(60) Provisional application No. 60/042,472, filed on Mar. 28, 1997.

(51) Int. Cl.7 .................................................. A61B 1/32
(52) U.S. Cl. ...................... 600/205; 600/206; 600/229; 600/232
(58) Field of Search .......................... 600/235, 227, 600/228, 229, 231, 232, 233, 210, 206, 205, 201

(56) References Cited

U.S. PATENT DOCUMENTS

| | | | |
|---|---|---|---|
| 5,727,569 A | | 3/1998 | Benetti et al. |
| 5,836,311 A | | 11/1998 | Borst et al. |
| 5,865,730 A | | 2/1999 | Fox et al. |
| 5,875,782 A | * | 3/1999 | Ferrari et al. ............ 600/235 X |
| 5,885,271 A | | 3/1999 | Hamilton et al. |
| 5,891,017 A | | 4/1999 | Swindle et al. |
| 5,894,843 A | * | 4/1999 | Benetti et al. ........... 600/201 X |
| 5,947,896 A | * | 9/1999 | Sherts et al. ............. 600/233 X |
| 5,967,972 A | * | 10/1999 | Santilli et al. ........... 600/235 X |
| 5,967,973 A | * | 10/1999 | Sherts et al. ............. 600/205 X |
| 6,036,641 A | * | 3/2000 | Taylor et al. ............ 600/235 X |
| 6,132,370 A | * | 10/2000 | Furnish et al. ............... 600/235 |

* cited by examiner

*Primary Examiner*—Jeffrey A. Smith
(74) *Attorney, Agent, or Firm*—Rankin, Hill, Porter & Clark LLP

(57) ABSTRACT

A stabilizer for use in surgical procedures such as coronary bypass surgery includes an elongate, rigid handle, a neck at the end of the handle, a base leg connected to the end of the neck, and first and second spaced, generally flat fingers that are disposed generally parallel with each other and which lie in a plane disposed at an angle from the longitudinal axis of the handle. The fingers can be used to press against the surface of the heart to stabilize it during surgery. In another embodiment, the handle is in the form of a flexible member that can be adjusted in a variety of positions. In either embodiment, the attachment between the fingers and the heart can be enhanced by providing serrations for the underside of the fingers, or by making the fingers hollow and forming a plurality of openings in the underside of the fingers in order to apply a vacuum to the underside of the fingers.

20 Claims, 14 Drawing Sheets

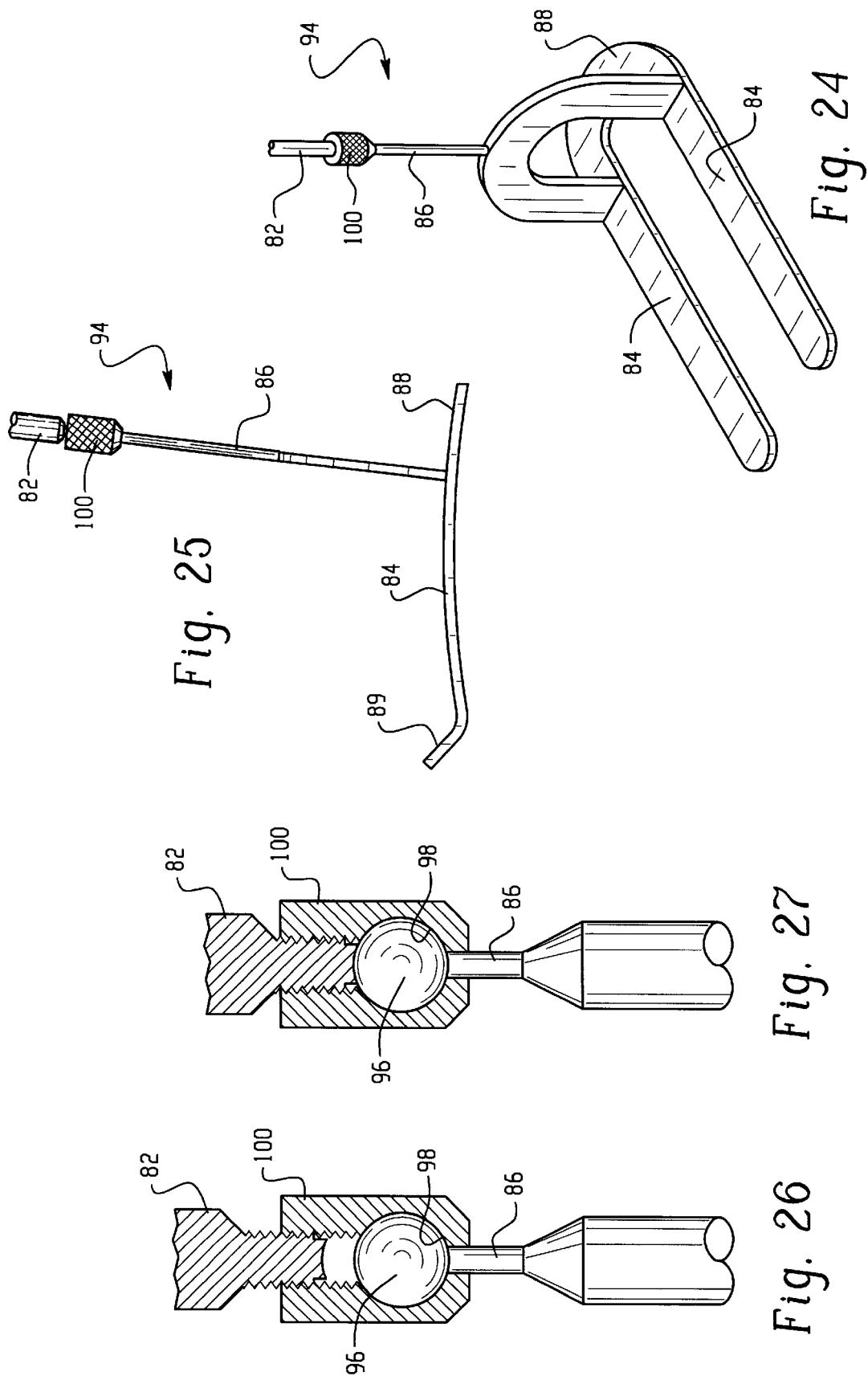

SURGICAL STABILIZER

This application is a continuation of application Ser. No. 09/049,597, filed Mar. 27, 1998, now U.S. Pat. No. 5,967,972, which claims priority from provisional application No. 60/042,472, filed Mar. 28, 1997.

BACKGROUND OF THE INVENTION

1. Field of the Invention

The invention relates to retractors that are used in various types of surgeries such as cardiovascular surgery and, more particularly, to a retractor that permits such operations to be conducted with minimal trauma to the patient.

2. Reference to Provisional Application

Reference is made to provisional application Ser. No. 60/042,472, filed Mar. 28, 1997, the disclosure of which is incorporated herein by reference and from which priority is claimed.

3. Description of the Prior Art

In the course of such operative procedures as mitral valve surgery, it is necessary to expose the heart. Such exposure traditionally has been accomplished by performing a sternotomy (cutting an incision completely through the sternum and retracting the sternum). The retraction is accomplished by a retractor that employs parallel grips that engage the edges of the separated sternum. The grips are mounted perpendicularly to a toothed crossbar. One of the grips is fixed to one end of the crossbar, while the other grip is movably mounted to the crossbar by means of a pinion that engages the teeth of the crossbar. Upon rotating the pinion, the movable grip can be moved away from the fixed grip, thereby retracting the sternum so as to expose the heart. A retractor of the type described is shown in U.S. Re. 34,150, issued Dec. 29, 1992 to A. E. Santilli and D. M. Cosgrove III ("the '150 patent"), the disclosure of which is incorporated herein by reference.

After the sternum has been retracted, it is necessary to retract portions of the heart in order to expose diseased or defective parts thereof. Such retraction has been accomplished by attaching a cardiovascular retractor to one of the grips of the sternum retractor. The cardiovascular retractor, in preferred form, includes a horizontal rod to which retractor blades having elongate handles are attached by means of universal clamps. The rod is spaced above the grip a considerable distance in order to permit the blades to have access to the heart at a favorable angle. The blades can be moved so as to engage portions of the heart to be retracted. Thereafter, upon pulling the blades and locking them in place by tightening the universal clamps, the heart can be retracted in any manner desired and maintained in that position as long as necessary.

The blades in the described construction can be moved back and forth, up and down, side to side, and they can be pivoted about the longitudinal axis of the handle. Such versatility enables the device to be used for virtually any type of heart operation where retraction is required. A preferred example of the device in question is disclosed in the '150 patent.

While the retractor disclosed in the '150 patent is effective for retraction of the sternum and subsequent retraction of the heart, unfortunately the operative technique is very invasive. That is, the splitting of the sternum coupled with its retraction is an extremely traumatic procedure. The recovery time from such a procedure can be significant. Further, the patient will experience considerable pain and discomfort during the recovery process. It is possible that the trauma associated with the process can have a negative impact on the patient's recovery from the operation.

Desirably, a retractor would exist that would permit surgical procedures to be performed that are less invasive than are possible with presently available retractors. Preferably, any such retractor would be relatively small and lightweight compared with prior retractors.

SUMMARY OF THE INVENTION

In accordance with the present invention, a new and improved retractor is disclosed that is minimally invasive. The invention also includes a new and improved method of retraction. By using the present invention, the heart can be accessed through a small incision between the ribs on the left side of the chest, usually between the third and fourth ribs. The right side of the chest also can opened in this manner for various purposes such as harvesting the right-side mammary artery. If it is desired to approach the heart through the sternum, only a small opening in the sternum is required. Further, the present invention permits certain heart operations to be performed without the need to stop the heart and use a heart-lung machine. In addition to heart surgeries, the present invention also enables other types of operations to be performed more effectively that has been possible heretofore.

The retractor according to the invention is provided in two embodiments for use in different surgical procedures as the surgeon may determine. In one embodiment, the retractor includes a pair of small grips, or paddles, that are mounted to an elongate crossbar. The grips are disposed at the ends of arms that are connected removably to blocks that are connected to the crossbar. One of the blocks is fixed to one end of the crossbar, while the other block is movable along the crossbar so as to move toward or away from the fixed grip. The movable block is moved along the crossbar by means of a pinion that engages teeth on the crossbar. The pinion has a handle (or wrench) in order to permit the block to be moved readily.

The crossbar in the present invention includes a hinge disposed at a location between its ends and between the spaced grips. The hinge is movable about an axis that is perpendicular to the longitudinal axis of the toothed portion of the crossbar and parallel to, or coincident with, a plane in which the toothed portion of the crossbar lies. Accordingly, the hinge enables one end of the crossbar to be pivoted which, in turn, enables the fixed grip to be pivoted relative to the movable grip. Preferably, the hinge enables the fixed grip to be moved through an angle of +45 degrees and −45 degrees relative to the longitudinal axis of the toothed portion of the crossbar.

The invention includes means for pivoting the fixed grip about the axis of the hinge. The means for pivoting can take two forms. In the first form, a first, vertically extending bracket is secured removably to one of the blocks and a second, vertically extending bracket is secured removably to the other block. An elongate rod having first and second opposed ends is pivotally connected at its first end to the first bracket and adjustably connected at its second end to the second bracket. Preferably, the second bracket includes an opening through which the second end of the rod extends. The second end of the rod is threaded and carries a nut for engaging the second bracket.

When the crossbar is positioned in a straight line, i.e., not pivoted, the rod is parallel to the longitudinal axis of the crossbar. The rod is connected to the brackets such that it is disposed above the crossbar a desired amount. When the nut is tightened and/or when the grips are moved apart, the fixed grip will be pivoted relative to the movable grip.

The invention also includes so-called side arm attachments. These attachments are elongate rods that can be removably attached to either of the arms. The rods enable one or more retractor blades of conventional design having elongate handles to be used to retract portions of the heart. Each retractor blade is connected to a selected rod by means of a universal clamp that encircles the handle of the blade and which is attached to the rod. Each clamp includes a nut that enables the clamp to be tightened or loosened with one hand. The clamps permit the blades to be moved to any position that may be desired by the surgeon.

The invention is especially effective for certain types of heart surgeries when employing a retractor blade known as a stabilizer. The stabilizer in question has an elongate handle to which a pair of spaced, parallel, generally flat fingers are connected at one end. The fingers lie in a plane disposed at an angle of approximately 125 degrees from the longitudinal axis of the handle. The stabilizer enables the heart to be compressed so as to be rendered relatively motionless. The region of the heart between the spaced-apart fingers will be relatively starved for blood, thereby permitting surgery to be performed without the need for a heart-lung machine to stop the heart. In order to accommodate different operative conditions, the stabilizer can be provided with malleable fingers, a malleable neck, or with an adjustable ball and socket connection between the handle and the fingers.

A particularly effective technique for supporting the stabilizer is to provide a housing that can be connected to a selected block. The stabilizer is connected to the housing by a flexible member that can be secured in a rigid position when desired. Preferably, the flexible member includes a plurality of generally tubular members disposed in end-to-end relationship, a cam disposed within the housing, a fitting (to which the stabilizer is connected) disposed at the end of the generally tubular members, and a cable extending through the generally tubular members. Upon activating the cam, the cable will be tightened or loosened, thereby securing the stabilizer in place or permitting it to be moved. An adjustment mechanism also can be provided for pretensioning the generally tubular members.

In a second embodiment of the invention, both blocks are movably mounted on the crossbar. This permits each arm with its respective grip to be positioned at any desired location relative to the hinge.

The invention also includes a second form of the means for pivoting the crossbar. The second form includes first and second brackets that are connected to the first and second blocks, respectively. The brackets are connected by a toothed rod, or rack, that is affixed to one of the brackets and which extends through an opening in the other bracket. The other bracket includes a pinion that can be rotated by a wingnut. A spring-biased pawl prevents the brackets from moving away from each other while permitting the brackets to move toward each other, thereby causing the crossbar to be pivoted.

The method according to the invention comprises a particular technique for retracting the patient's ribs or sternum most effectively. The method in question involves compressing the distal ribs, while retracting and raising the adjacent proximal ribs. This result is accomplished by orienting the crossbar such that the movable grip is on the distal side of the patient.

Initially, the hinge is positioned to provide a straight crossbar and the grips are moved together in order to insert them between the ribs. The means for pivoting is actuated in order to pivot the fixed, or proximal, grip about the axis of the hinge. Then, the grips are moved apart by moving the distal grip along the crossbar. As the distal grip is moved, the grips are spaced further apart and the proximal grip is raised even further. Such retraction provides adequate access to the heart despite the small incision between the ribs.

The retractor according to the invention can be used for operations on either side of the chest. By orienting the crossbar appropriately, the retractor can always be positioned to compress the distal ribs and retract and raise the proximal ribs. A similar result can be obtained with incisions through the sternum, that is, appropriate positioning of the blocks and brackets will enable either side of the sternum to be retracted and raised as may be desired.

As will be appreciated from the foregoing description, the retractor according to the invention is minimally invasive. By using the retractor according to the invention, adequate access to the heart can be obtained merely by making a small incision between two adjacent ribs. There is no need to completely split the patient's sternum in order to have access to the heart. The foregoing results are obtained by using very small grips and using the retractor first as a rib-spreader (or sternum, spreader) and then as a proximal rib-lifter (or sternum lifter). Once the ribs or sternum have been retracted and raised properly, various attachments can be connected to the retractor for purposes of cardiovascular retraction and other purposes.

The retractor according to the invention also can be used for other types of surgeries, such as spinal implant surgery. The retractor can be used for both anterior and posterior spinal implant surgery. The ability to pivot and displace the fixed grip relative to the movable grip is a significant advantage compared with existing retractors. Further, because the grip-carrying arms are removably connected to the retractor, it is possible to substitute differently configured grips to conduct different types of surgical procedures, to conduct surgical procedures on different sizes of people, or to perform different types of retractions during the course of the same surgical procedure. Such substitutions can be accomplished quickly and easily, thereby enhancing the versatility of the retractor.

The foregoing features and advantages will be apparent from the accompanying drawings and the description that follows.

BRIEF DESCRIPTION OF THE DRAWINGS

FIGS. 24, 25, 26, and 27 are perspective, side, and cross-sectional views, respectively, of another embodiment of a stabilizer according to the invention having a ball-and-socket adjustable neck.

DESCRIPTION OF THE PREFERRED EMBODIMENT

Figure 1:
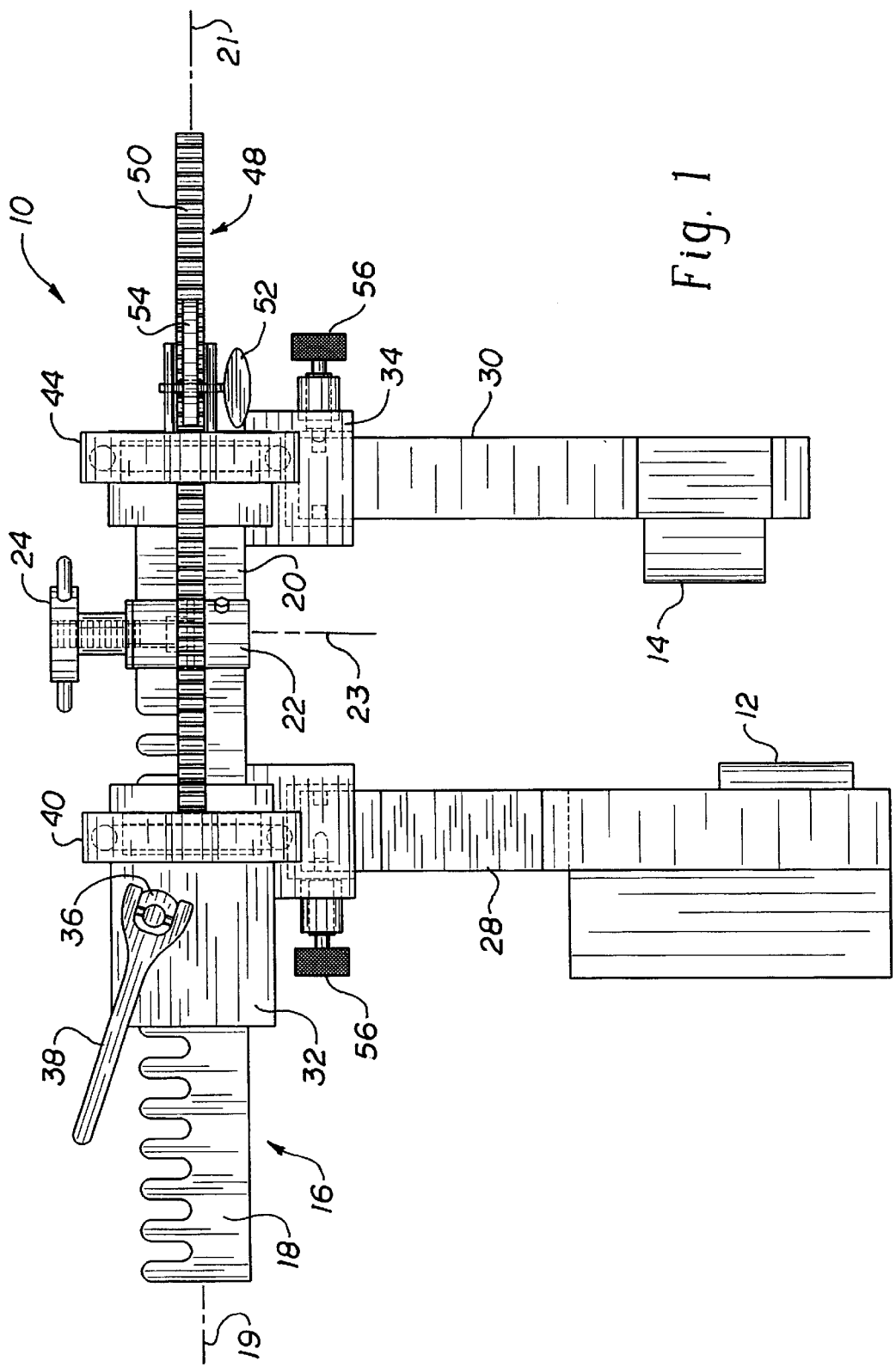
FIG. 1 is a top plan view of an assembled retractor according to the invention showing a movable block, a fixed block, and a toothed-rod pivoting device.
Figure 2:
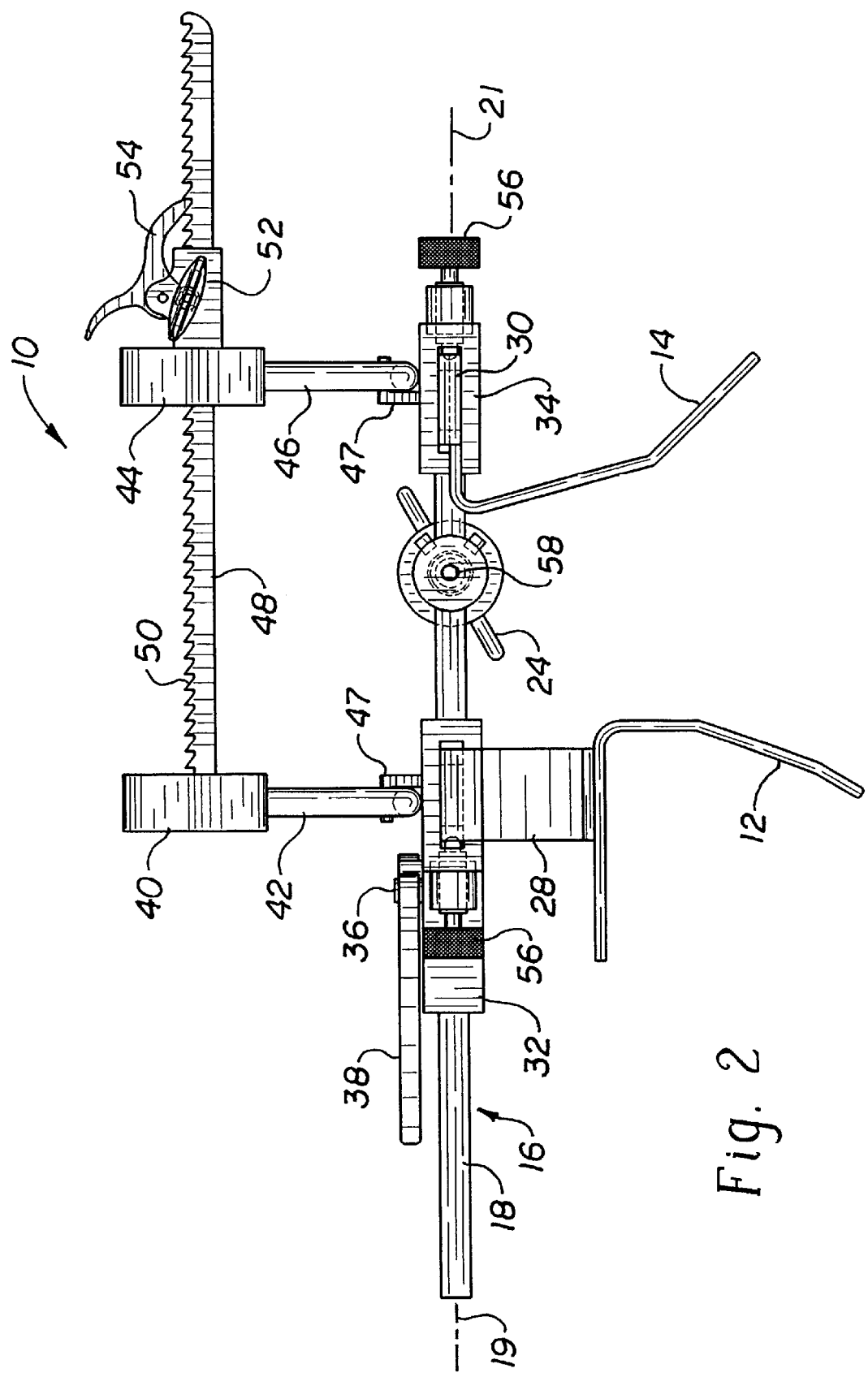
FIG. 2 is a front elevational view of the retractor of FIG. 1.
Figure 3:
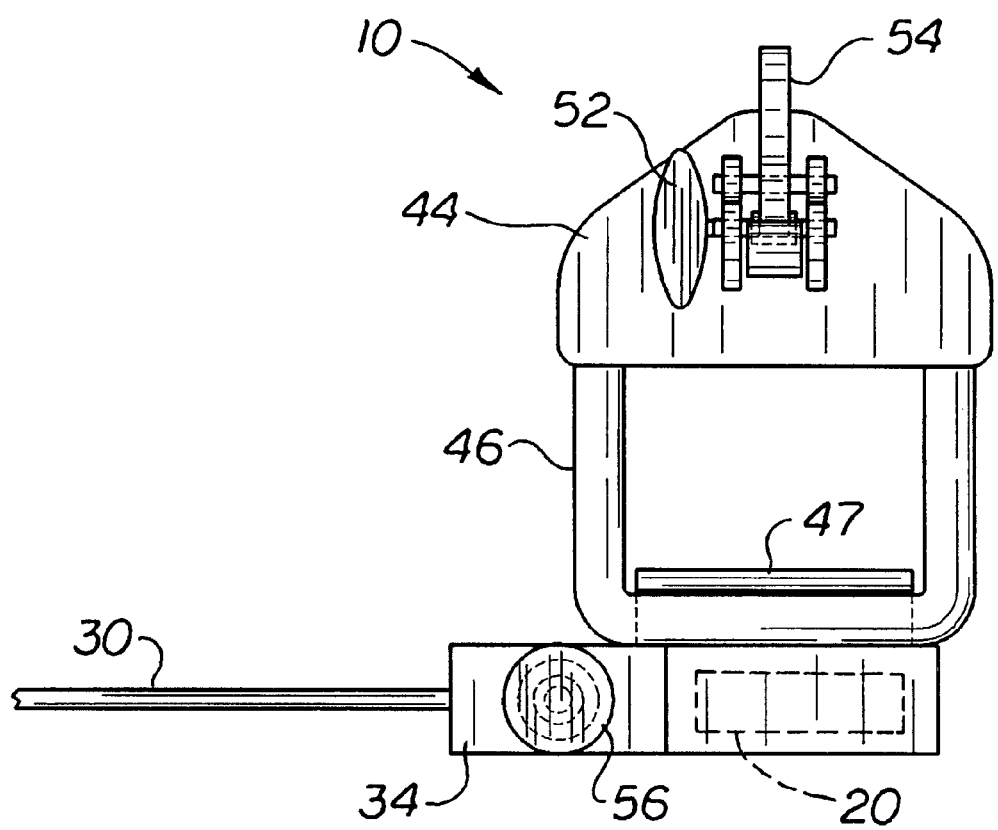
FIG. 3 is a side elevational view of the retractor of FIG. 1.
Figure 4:
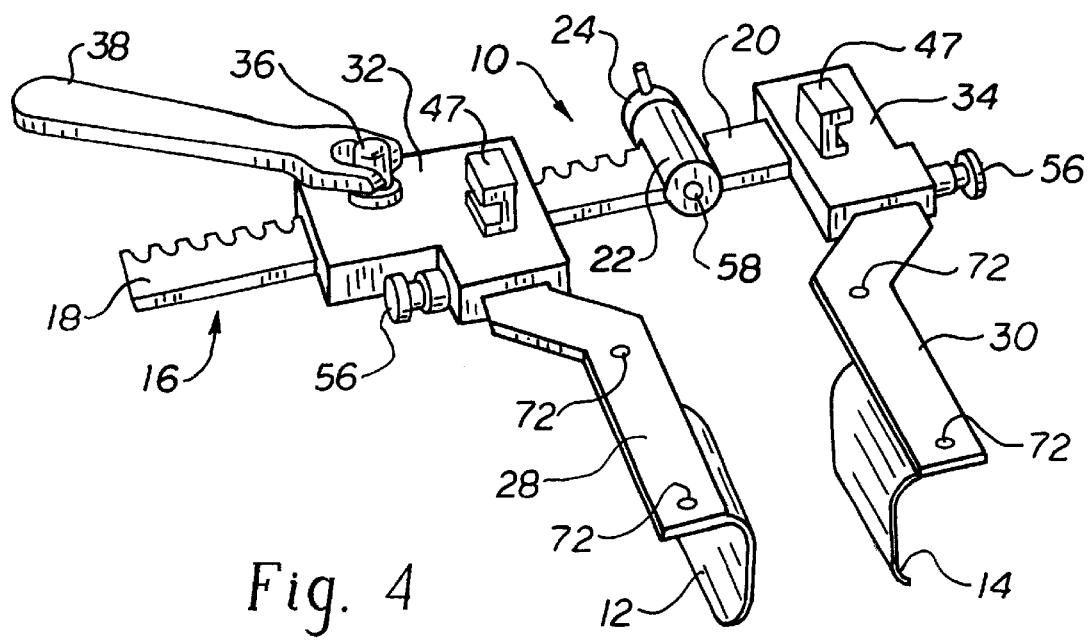
FIG. 4 is a perspective view of the retractor of FIG. 1 without a pivoting device and with different grips.

Referring particularly to FIGS. 1–3, a retractor according to the invention is indicated by the reference numeral 10. In the description that follows, reference should be made to the various other Figures, where appropriate, for a more detailed understanding of the individual components that are used with the invention.

The retractor 10 includes a pair of small, parallel grips 12, 14, or paddles, that are mounted to an elongate crossbar 16. The crossbar 16 includes a toothed portion 18 having a longitudinal axis 19 and a non-toothed portion 20 having a longitudinal axis 21. The crossbar 16 includes a locking, adjustable hinge 22 that connects the portions 18, 20 at a location between the spaced grips 12, 14. The hinge 22 pivots about an axis 23 that is perpendicular to the longitudinal axis 19 of the portion 18 and parallel to, or coincident with, a plane in which the axis 19 lies.

The hinge 22 enables the portion 20 to be pivoted relative to the portion 18 which, in turn, enables the grip 14 to be pivoted relative to the grip 12. Preferably, the hinge 22 enables the grip 12 to be moved through an angle of +45 degrees and -45 degrees relative to the longitudinal axis 19. The hinge 22 includes a lock 24 that can be tightened to prevent movement of the hinge 22 when a desired position of the grips 12, 14 has been attained.

The grips 12, 14 are disposed at the ends of arms 28, 30 that extend away from the crossbar 16. The arms 28, 30 are connected removably to blocks 32, 34, respectively, that are connected to the portions 18, 20. The block 34 is fixed to the portion 20, while the block 32 is movable along the portion 18 so as to move the grip 12 toward or away from the grip 14. Movement of the block 32 is accomplished by a pinion 36 that engages the teeth of the portion 18. A handle 38 is provided to rotate the pinion 36.

The invention includes a pivoting device for pivoting the grip 14 about the axis 28 of the hinge 26. The pivoting device in the preferred embodiment includes a first, vertically extending bracket 40 having a U-shaped 3/16 inch steel rod 42. A second, vertically extending bracket 44 also has a U-shaped 3/16 inch steel rod 46. The term "vertically" is used herein for purposes of convenience of description only. It is to be understood that the retractor 10 can be oriented in different positions, and the use of such terms of orientation as "vertically" is not to be construed as a limitation on the possible uses or orientations of the retractor 10.

The upper surfaces of the blocks 32, 34 each include an upside-down L-shaped bar 47. The bars 47 are welded or otherwise secured to the upper surfaces of the blocks 32, 34. The bars 47 are aligned along axes parallel to the axis 23 of the hinge 22, i.e., perpendicular to the longitudinal axes 19, 21. The undercut portions of the bars 47 face away from each other. The undercut portions are large enough to receive the rods 42, 46.

An elongate rod 48 is securely connected at one end to the first bracket 40. The second bracket 44 includes an opening through which the other end of the rod 48 extends. The upper surface of the rod 48 has a plurality of teeth 50. The bracket 44 includes a pinion that is operated by a wingnut 52. The pinion engages the teeth 50. A spring-biased pawl 54 also engages the teeth 50. As will be apparent from an examination of FIG. 2, the pawl 54 permits the brackets 40, 44 to be moved toward each other without interference, but prevents the brackets 40, 44 from being moved away from each other (unless released). When the lock 24 is loosened, the wingnut 52 can be rotated to cause the brackets 40, 44 to come closer together, thereby causing the grip 14 to be pivoted relative to the grip 12.

The blocks 32, 34 include slots adapted to receive the arms 28, 30. The arms 28, 30 are retained in the slots by notches (FIG. 9) that are engaged by spring-biased pins 56 included as part of the blocks 32, 34. Upon retracting the pins 56, the arms 28, 30 can be removed. Accordingly, the grips 12, 14 can be replaced quickly and conveniently by grips suited for other purposes. Grips of different configurations for different surgical procedures are shown in FIGS. 4–9. Some of the distal grips (FIGS. 5 and 9) includes malleable upper portions with rectangular openings that can be moved to different positions as the surgeon deems necessary.

The retractor 10 includes an external lock 60 for the crossbar 16. Referring to FIGS. 4 and 6–8, the lock 60 includes a plurality of prongs 62 that are fitted over the crossbar 16 on either side of the hinge 22. The prongs 62 extended from a base plate 64 having an opening therein. A threaded pin 66 extends through the opening and into an opening 58 included as part of the hinge 22 in order to securely attach the lock 60 to the crossbar 16.

A rod 68 (FIGS.7 and 10) can be attached to either of the arms 28, 30. The rod 68 preferably is L-shaped, although other configurations are possible. The rod 68 includes a pair of small pins 70 that project form one side thereof. The arms 28, 30 each include a pair of spaced openings 72 in the upper surfaces thereof (FIGS. 4–9). The pins 70 can be fitted into the openings 72 to attach the rod 68 to one of the arms 28, 30.

Figure 7:
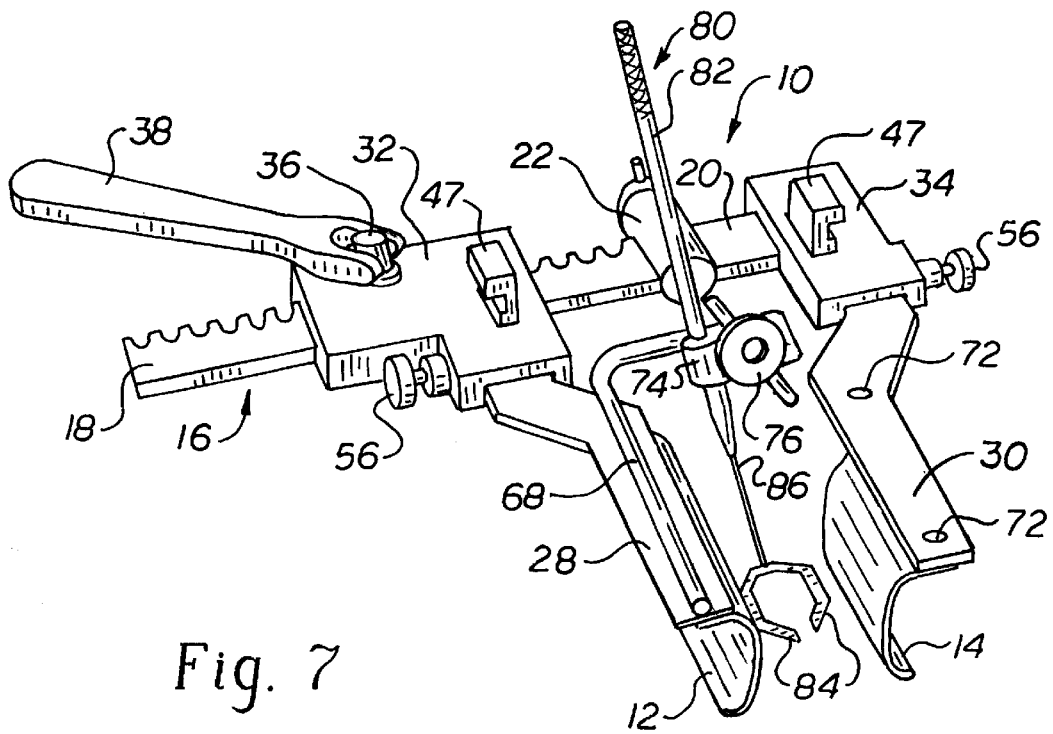
FIG. 7 is a perspective view of the retractor of FIG. 1 without a pivoting device and with a stabilizer held in place by a clamp that is connected to an arm-mounted rod.
Figure 8:
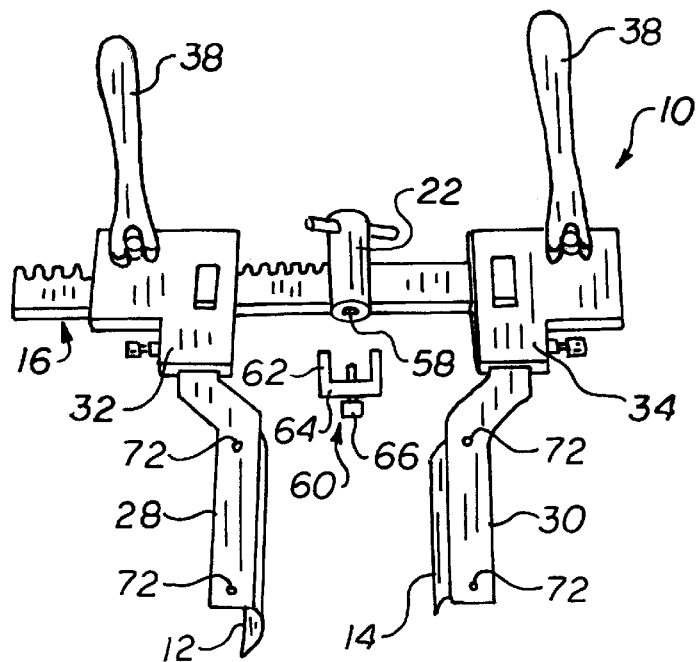
FIG. 8 is a perspective view of the retractor according to the invention showing two grips being supported by movable blocks and a lock for connecting portions of a crossbar.

The rod 68 enables one or more retractor bladed of conventional design having elongated handles to be used to retract portions of the heart. Each retractor blade is connected to the rod 68 by means of a universal clamp 74 that encircles both the handle of the blade and the rod (FIG. 7). Each clamp 74 includes a nut 76 that enables the clamp 74 to be tightened or loosened with one hand. The clamps 74 permit the blades to be moved to any position that may be desired by the surgeon and quickly and easily locked in place there. Force applied to the rod 68 by the retractor blade and the clamp 74 biases the pins 70 in the openings 72, thereby preventing the rod 68 from being dislodged.

The invention is effective with a particular type of retractor blade 80 known as a stabilizer. Referring to FIGS. 7 and 18–20, one form of the stabilizer 80 had an elongate handle 82 to which a pair of spaced, parallel, generally flat fingers 84 are connected at one end. The fingers 84 lie in a plane disposed at an angle of approximately 125 degrees from the longitudinal axis of the handle 82 (see FIG. 19). The fingers 84 are connected to the handle 82 by a malleable neck 86 and a base leg 88, thus permitting the angular relationship between the fingers 84 and the handle 82 to be changed as the surgeon may see fit. If desired, the fingers 84 also can be made of a malleable material for purposes of adjustment. The underside of the fingers 84 are serrated and distal ends 89 are angled toward each other. The retractor blade 80 enables the heart to be compressed. The region of the heart between the spaced apart fingers 84 will be relatively starved for blood, thereby permitting surgery to be performed without the need for a heart-lung machine to stop the heart.

Figure 21:
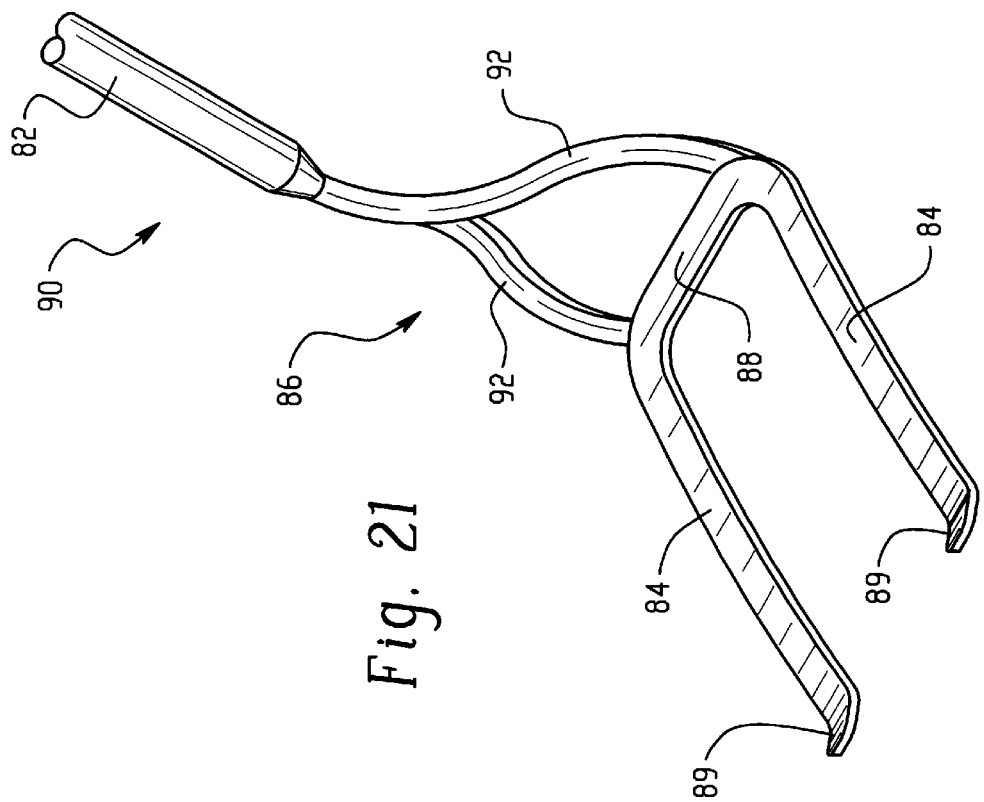
FIGS. 21, 22, and 23 are perspective, side, and bottom views, respectively, of another embodiment of a stabilizer according to the invention having a rigid neck.
Figure 22:
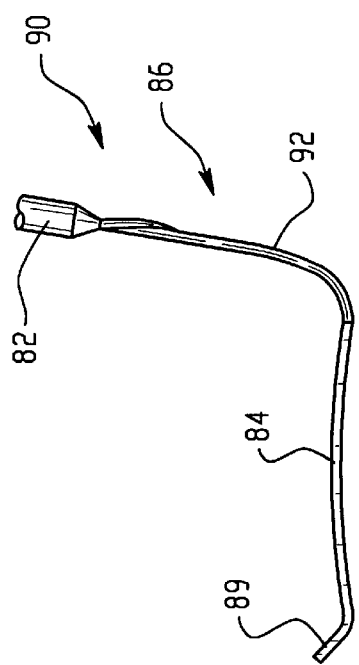
Figure 23:
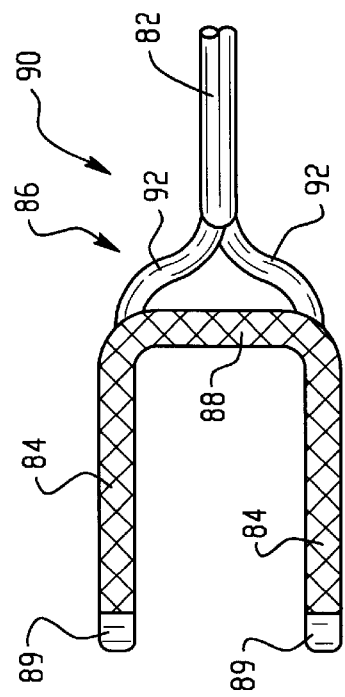

Another form of the stabilizer 80 is shown in FIGS. 21–23, and is identified by the reference numeral 90. The stabilizer 90 shown if FIGS. 21–23 is similar to the stabilizer shown 80 in FIGS. 7 and 18–20, except that the neck is not malleable. The neck 86 includes two portions 92 that provide extra support for the fingers 84. Also, the distal ends 89 are inclined upwardly from the plane in which the fingers 84 lie.

Yet another form of the stabilizer 80 is shown in FIGS. 24–27, and is identified by the reference numeral 94. In this version of the stabilizer 80, the neck 86 includes a ball 96 that is fitted into a socket 98 included as part of a threaded sleeve 100. The sleeve 100 is threaded onto the end of the handle 82 in order to compress the ball 96 within the socket 98. By tightening or loosening the sleeve 100, the ball 96 will be compressed or released. In turn, the position of the fingers 84 relative to the handle 82 can be adjusted as the surgeon may deem necessary.

Figure 10:
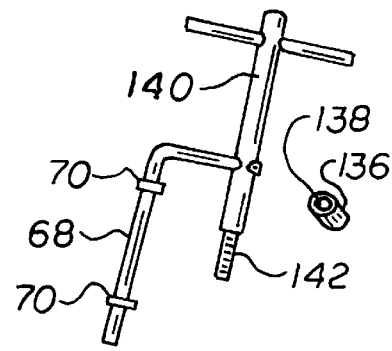
FIG. 10 is a perspective view of an L-shaped rod with pins for attachment to a block-mounted arm, a pinion for activating a block, and a wrench for the pinion.
Figure 9:
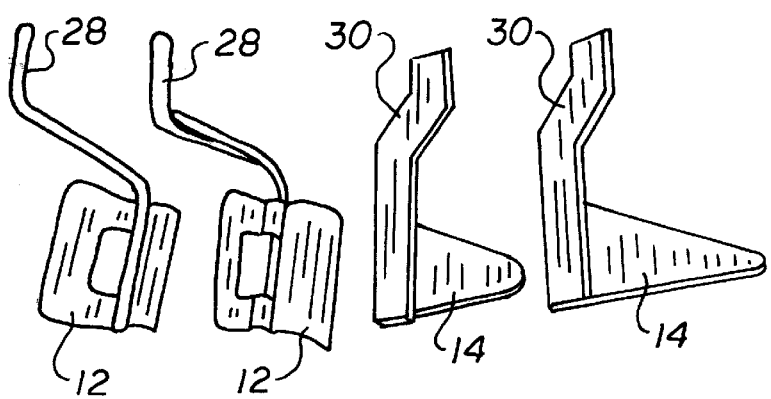
FIG. 9 is a perspective view showing various grips usable with the invention.
Figure 11:
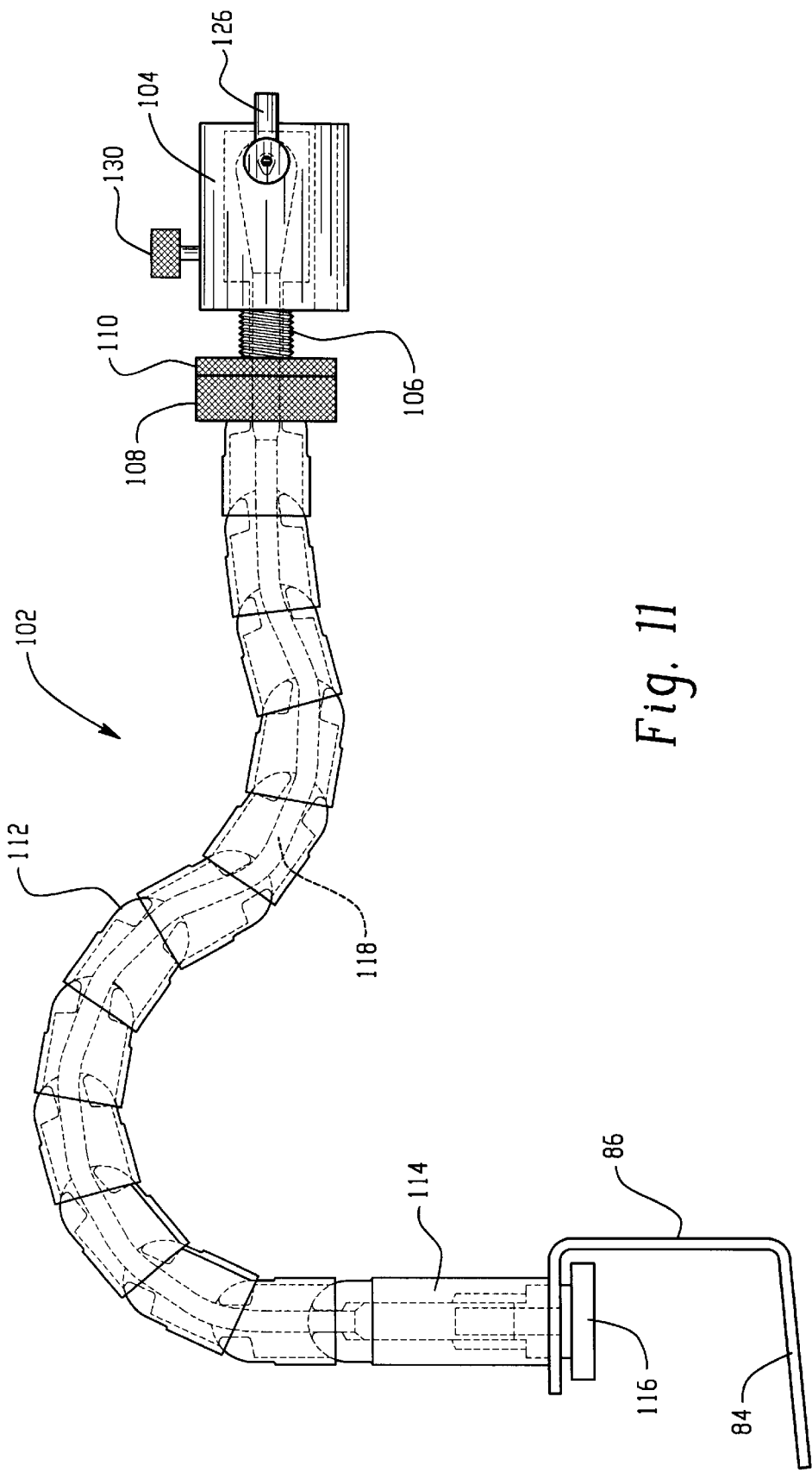
FIG. 11 is a side elevational view of a retractor in the form of a stabilizer and a flexible holder therefor in accordance with the invention.
Figure 12:
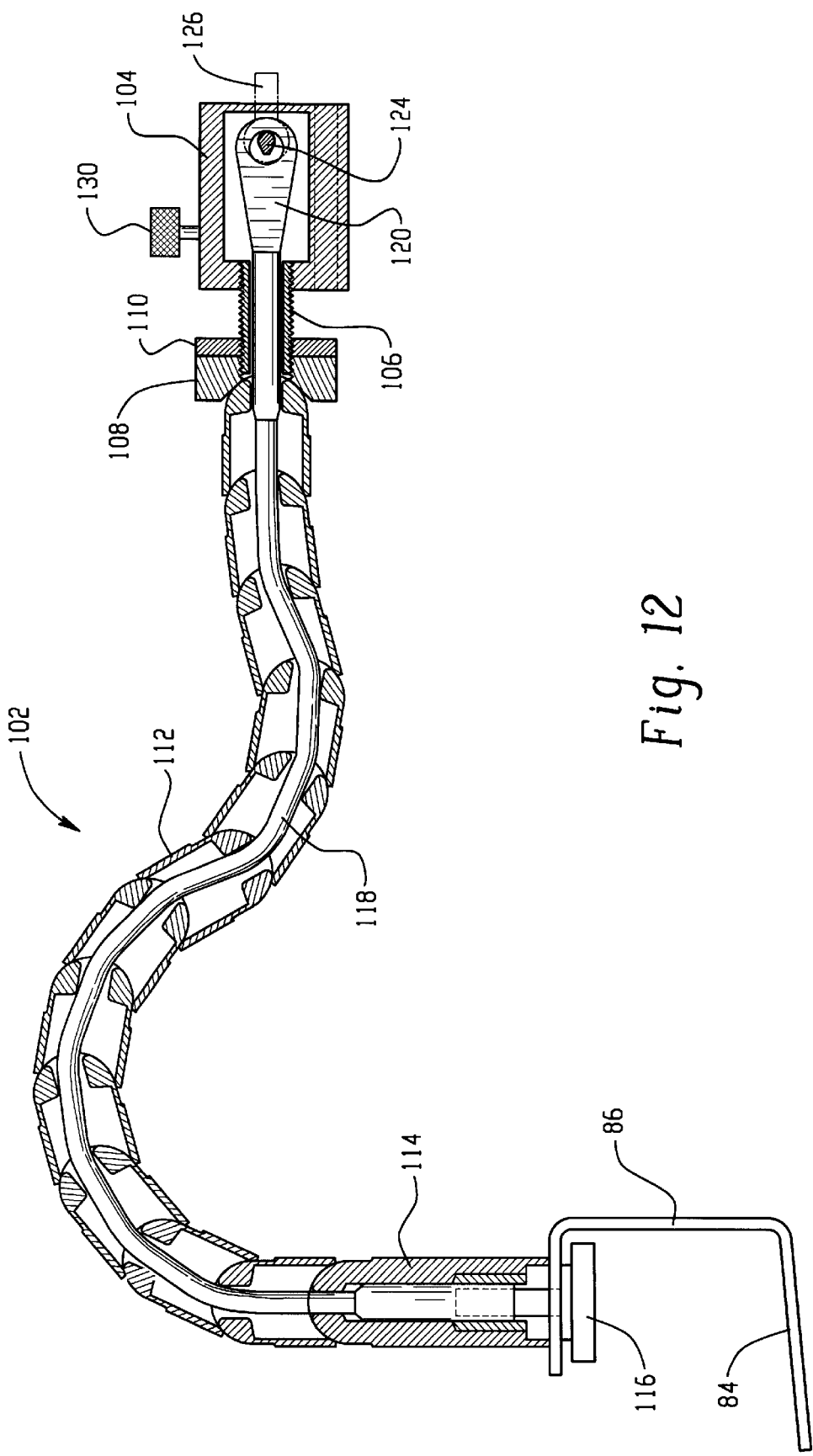
FIG. 12 is a cross-sectional view of the holder of FIG. 11.
Figure 13:
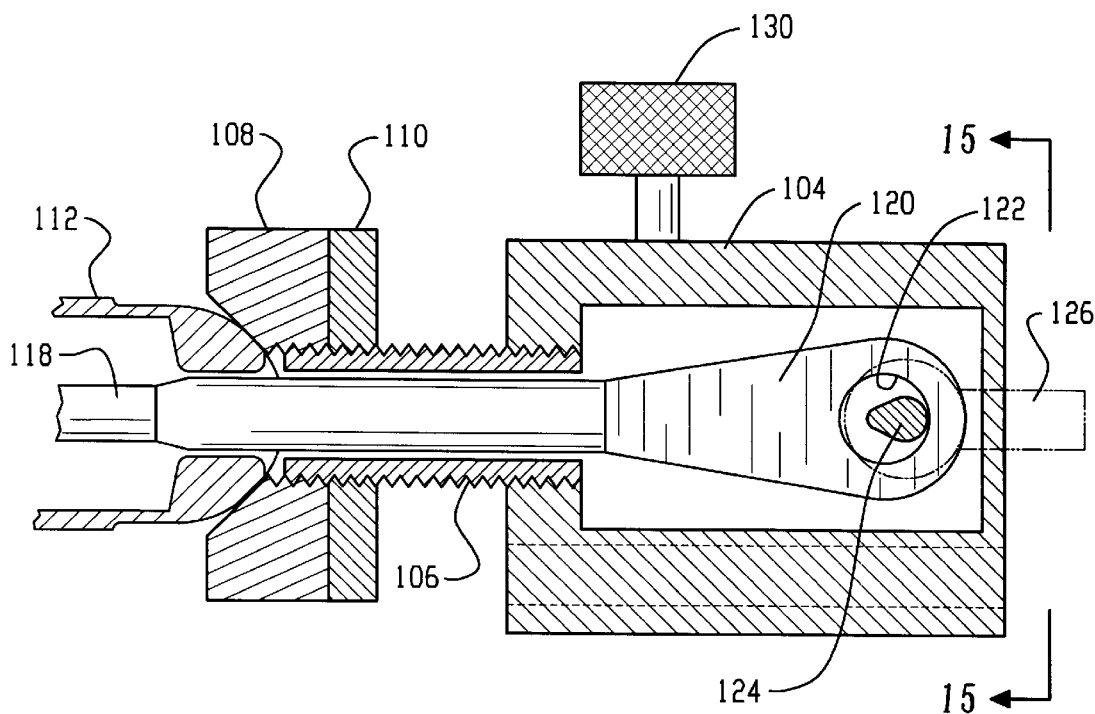
FIGS. 13 and 14 are cross-sectional views of a portion of the holder of FIG. 11 showing a cable-tightening cam in tightened and loosened positions.
Figure 14:
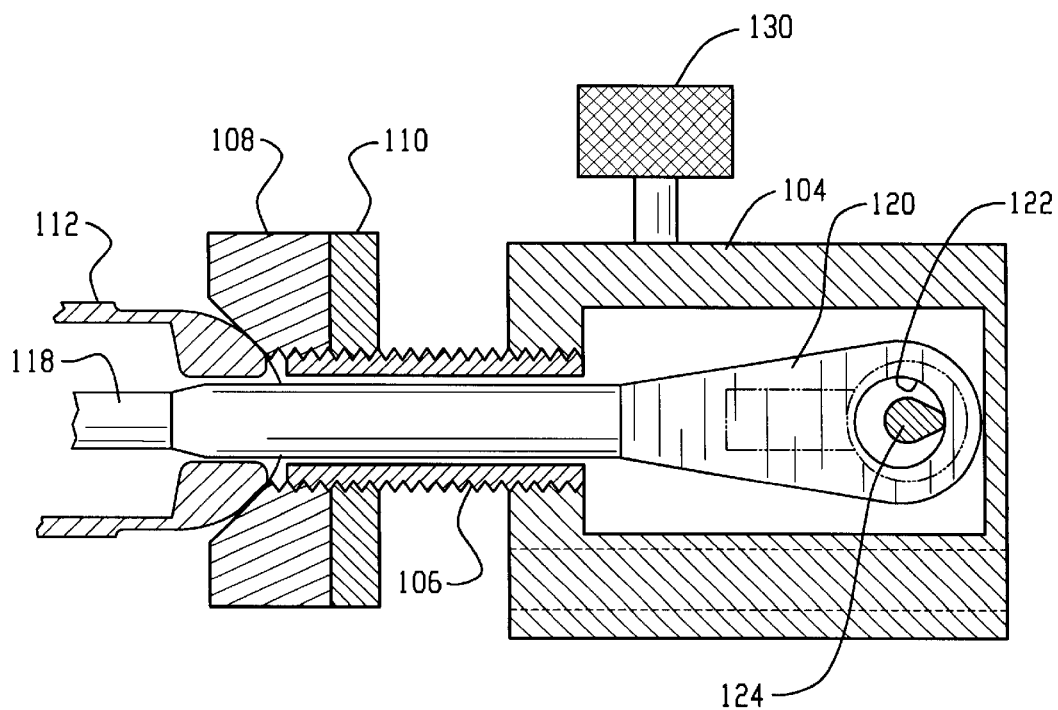

The various stabilizer versions described heretofore include a handle 82 that can be connected to the rod 68 shown in FIGS. 7 and 10 by means of a universal clamp 74. Yet another version of the stabilizer 80 is shown in FIGS. 6 and 11–17, and is identified by the reference numeral 102. The stabilizer 102 is connected to the retractor 10 by a different technique. In this version of the stabilizer 80, a selectively flexible connection between the neck 86 and a selected block 32, 34 is established. The connection includes a housing 104 from which a threaded fitting 106 extends. A nut 108 and a locknut 110 are threaded onto the fitting 106. A plurality of generally tubular members 112 are disposed in end-to-end relationship. The neck 86 of the stabilizer 102 is connected to a fitting 114 at the end of the tubular members 112 by means of a threaded pin 116. A cable 118 is connected to the fitting 114 and is threaded through the tubular members 112, through the fitting 106, and into the housing 104. The end of the cable includes a formation 120 having an opening 122 therein. A cam (eccentric) 124 is disposed within the opening 122 (FIGS. 13 and 14). A handle 126 is connected to the cam 124 and is disposed outside the housing 104.

Figure 15:
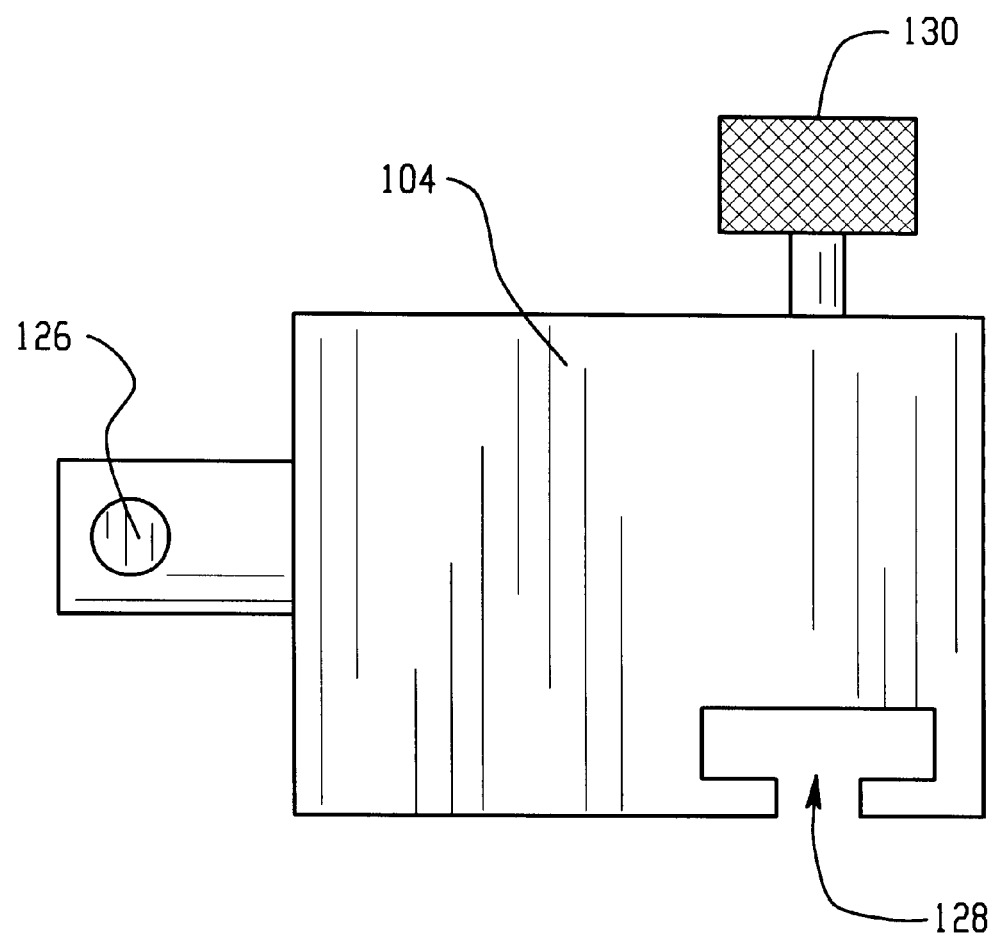
FIG. 15 is an end view of the holder of FIG. 11 taken along a plane indicated by line 15—15.

Referring to FIG. 15, the housing 104 includes a longitudinally extending "T-slot" 128 that opens through the lower face of the housing 104. The T-slot 128 can be fitted over one of the bars 47 and secured there by tightening a set screw 130 that opens into the upper portion of the T-slot 128. As will be apparent from an examination of FIGS. 11–15, the tension on the cable 118, and hence the compression force applied to the tubular members 112, can be pre-set by adjusting the nut 108 and the locknut 110 that are threaded onto the fitting 106 projecting from the housing 104. Thereafter, the tension on the cable 118 can be increased even more by rotating the handle 126 to move the cam 124 and the formation 120.

Figure 16:
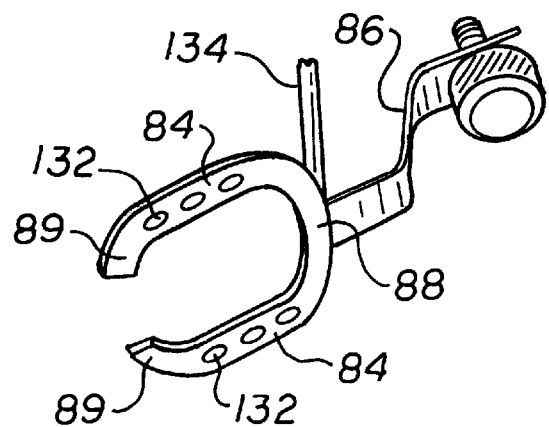
FIG. 16 is a perspective view of another embodiment of a stabilizer having a suction capability.
Figure 17:
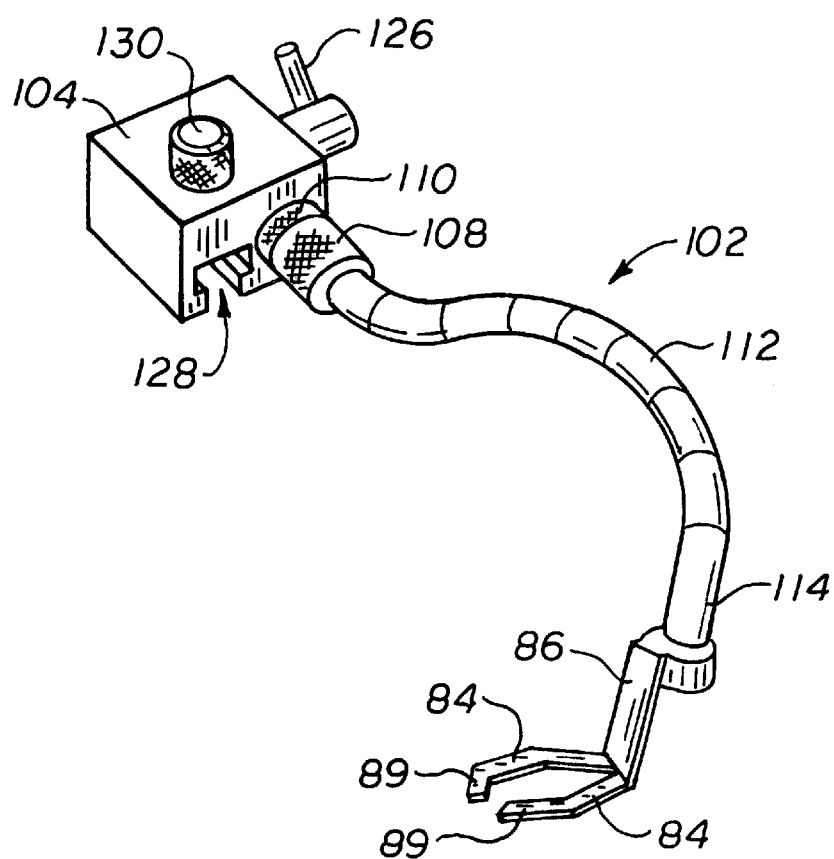
FIG. 17 is a perspective view of the stabilizer of FIG. 11.
Figure 18:
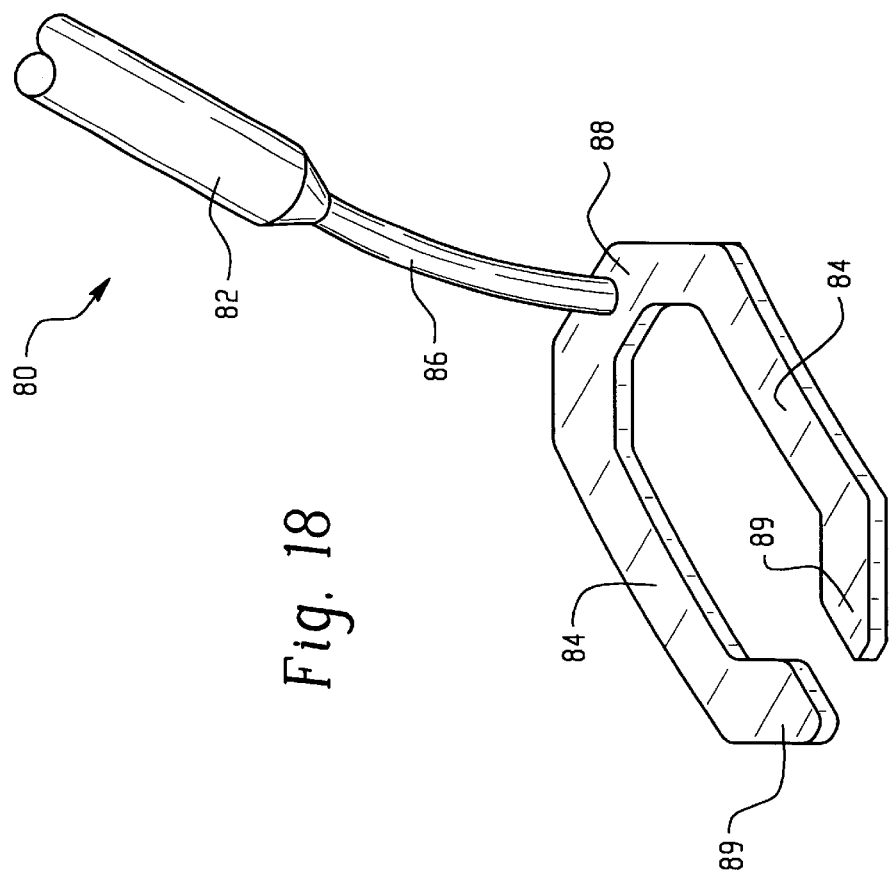
FIGS. 18, 19, and 20 are perspective, side, and bottom views, respectively, of a stabilizer according to the invention having a malleable neck.
Figure 19:
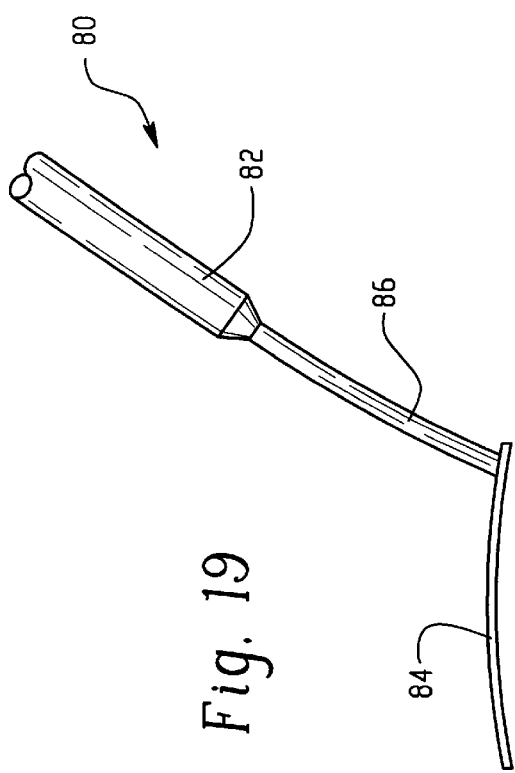
Figure 20:
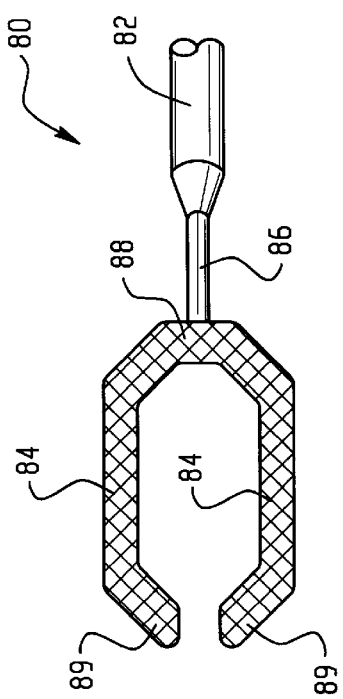

Referring particularly to FIG. 16, the fingers 84 can be made hollow with openings 132 on the underside. A hollow tube (or handle) 134 is connected to the fingers. A vacuum can be applied to the fingers 84 through the tube (or handle) 134 in order to withdraw blood or other fluids through the openings 132 in the fingers 84.

Referring to FIG. 10, an extra pinion 136 is shown. The pinion 136 includes a drive opening in the form of a hexagonal socket 138. The invention also includes a wrench 140 having a hexagonal end 142 for establishing a driving connection with the pinion 136. If desired, the handles and pinions 36, 38 shown in FIG. 8 can be removed from the blocks 32, 34 upon advancing the blocks 32, 34 beyond the ends of the crossbar 16 (to disengage the teeth). At that point, the pinions 36, with handles 38 attached, can be removed from the blocks 32, 34. Then, pinion 136 as shown in FIG. 10 can be inserted into the blocks 32, 34. The wrench 140 then can be used to move the blocks 32, 34 back and forth on the crossbar 16. The use of this unobtrusive pinion 136 is preferred in situations where space is at a premium or the handles 38 otherwise might be considered to be obstructive.

Figure 5:
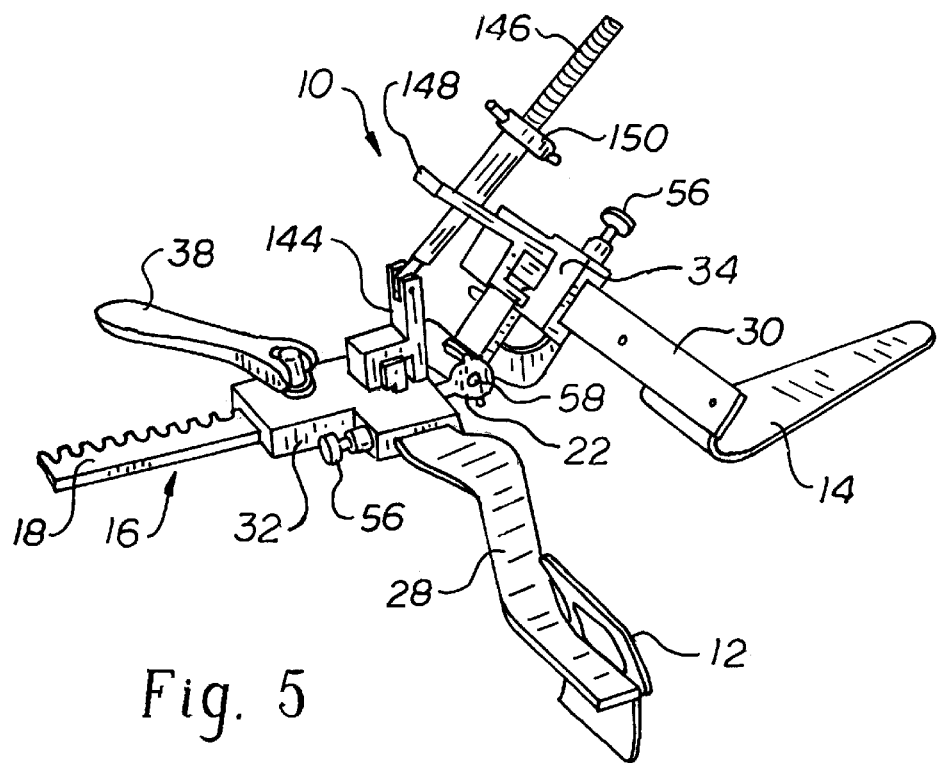
FIG. 5 is a perspective view of the retractor of FIG. 1 with a threaded-rod pivoting device and different grips.
Figure 6:
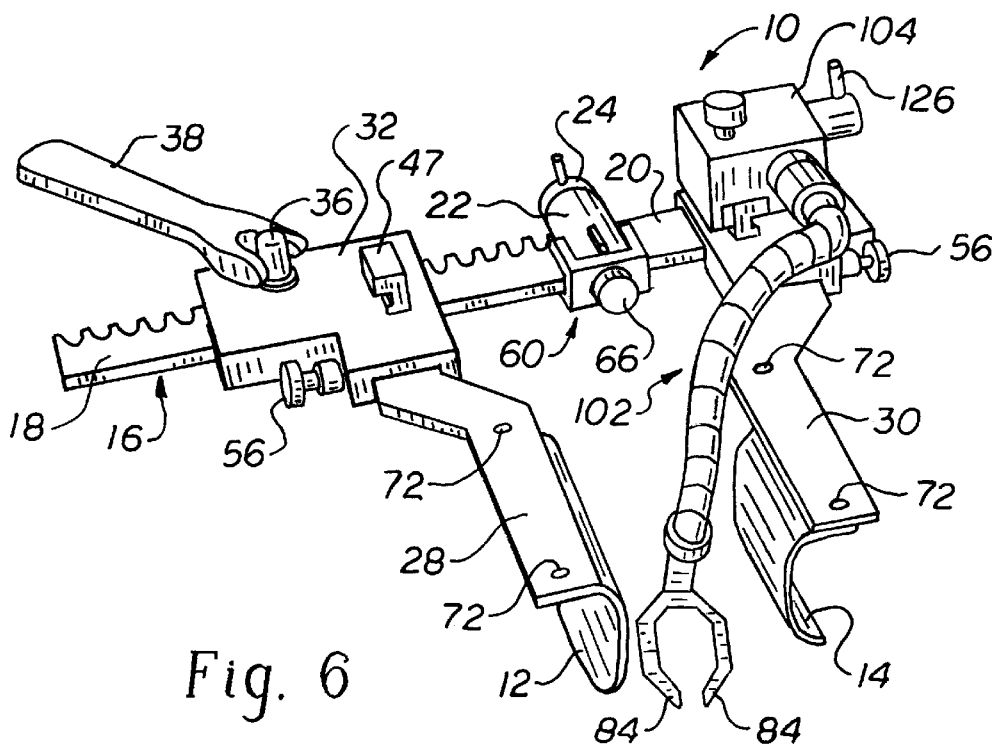
FIG. 6 is a perspective view of the retractor of FIG. 1 without a pivoting device and with a stabilizer held in place by a selectively flexible holder.

Referring now to FIG. 5, another form of pivoting device is shown. The device includes a first bracket 144 extending vertically upwardly from the block 32 to which an elongate, threaded rod 146 is pivotally connected at the upper end thereof. A second bracket 148 is connected to the block 34 and extends vertically upwardly therefrom. The second bracket 148 includes an opening through which the rod 146 extends. A nut 150 is threaded onto the rod 146. The opening is rounded on that side engaged by the nut 150. The nut 150 also is rounded on that end which engages the bracket 148.

As will be apparent from an examination of FIG. 5, tightening or loosening of the nut 150 will cause the brackets 144, 148 to be moved closer to each other or further apart. In turn, the grips 12, 14 will be pivoted relative to each other. That portion of the rod 146 that extends between the brackets 144, 148 is largely unthreaded. Accordingly, the rod 146 can receive retractor blade-supporting clamps 74 at a location between the brackets 144, 148. This feature provides an extra degree of versatility for the surgeon.

The method according to the invention comprises a particular technique for retracting the patient's ribs or sternum most effectively. The method in question involves compressing the distal ribs (usually the fourth and fifth ribs), while retracting and raising the adjacent proximal ribs (usually the second and third ribs). This result is accomplished by orienting the crossbar 16 such that the movable grip 12 is on the distal side of the patient.

Initially, the hinge 22 is positioned to provide a straight crossbar and the grips 12, 14 are moved together in order to insert them between the ribs. The means for pivoting is actuated in order to pivot the fixed, or proximal, grip 14 about the axis of the hinge 22. Then, the grips 12, 14 are moved apart by moving the distal grip 12 along the crossbar 16. As the distal grip is moved, the grips 12, 14 are spaced further apart and the proximal grip 14 is raised even further. Such retraction provides adequate access to the heart despite the small incision between the ribs.

The retractor 10 according to the invention can be used for operations on either side of the chest. By orienting the crossbar 16 appropriately, the retractor 10 can always be positioned to compress the distal ribs and retract and raise the proximal ribs. A similar result can be obtained with incisions through the sternum, that is, appropriate positioning of the blocks 32, 34 and brackets 40, 44 will enable either side of the sternum to be retracted and raised as may be desired.

As will be appreciated from the foregoing description, the retractor 10 according to the invention is minimally invasive. By using the retractor 10 according to the invention, there is no need to perform a full sternotomy in order to have access to the heart. The foregoing results are obtained by using very small grips 12, 14 and using the retractor first as a rib-spreader and then as a proximal rib-lifter. Once the ribs have been retracted and raised properly, various attachments can be connected to the retractor 10 for purposes of cardiovascular retraction and other purposes.

The retractor 10 according to the invention also can be used for other types of surgeries, such as spinal implant surgery. The retractor 10 can be used for both anterior and posterior spinal implant surgery. The ability to pivot the grips 12, 14 relative to each other is a significant advantage compared with existing retractors. Further, because the grip-carrying arms 28, 30 are removably connected to the retractor 10, it is possible to substitute different grips 12, 14 to conduct different types of surgical procedure. Such substitutions can be accomplished quickly and easily, thereby enhancing the versatility of the retractor.

Although the invention has been described in its preferred form with a certain degree of particularity, it will be understood that the present disclosure of the preferred embodiment has been made only by way of example and that various changes may be resorted to without departing from the true spirit and scope of the invention as hereinafter claimed. It is intended that the patent shall cover, by suitable expression in the appended claims, whatever features of patentable novelty exist in the invention disclosed.

What is claimed is:

1. A surgical stabilizer, comprising:
an elongate handle having a longitudinal axis and distal and proximal ends;
a neck made of a malleable material connected to and extending from the distal end of the handle, the neck having a distal end and a proximal end, the proximal end being connected to the distal end of the handle;
a base leg having first and second ends, the base leg being connected to the distal end of the neck;
first and second spaced, generally flat, hollow fingers having serrations and a plurality of openings on their underside, the fingers being disposed generally parallel with each other and lying in a plane disposed at an angle from the longitudinal axis of the handle, the first finger having a proximal end connected to the first end of the base leg and the second finger having a proximal end connected to the second end of the base leg; and
a hollow tube connected to the fingers, the hollow tube permitting a vacuum to be applied to the fingers.

2. The surgical stabilizer of claim 1, wherein the fingers are made of a malleable material.

3. The surgical stabilizer of claim 1, wherein the neck includes first and second portions that diverge from each other, the first portion being connected to the base leg adjacent the first end thereof, and the second portion being connected to the base leg adjacent the second end thereof.

4. The surgical stabilizer of claim 1, wherein the distal ends of the fingers are angled toward each other.

5. The surgical stabilizer of claim 1, wherein the distal ends of the fingers are inclined upwardly from the plane in which the fingers lie.

6. A surgical stabilizer, comprising:
a housing;
a flexible member having a distal end and a proximal end being connected to the housing, the flexible member capable of being tightened into a rigid position when desired;
a pair of spaced, generally flat, hollow fingers having serrations and a plurality of openings on their underside, the fingers being connected to the distal end of the flexible member; and
a hollow tube connected to the fingers, the hollow tube permitting a vacuum to be applied to the fingers.

7. The surgical stabilizer of claim 6, wherein the housing includes a slot by which the housing can be attached to a mounting bar.

8. The surgical stabilizer of claim 6, wherein the flexible member includes:
a plurality of generally tubular members disposed in end-to-end relationship;
a cam disposed within the housing;
a first fitting disposed at the distal end of the generally tubular members; and
a cable extending through the generally tubular members, the cable being connected at one end to the cam and being connected at the other end to the first fitting, activation of the cam causing the cable to be tightened or loosened.

9. The surgical stabilizer of claim 8, further comprising:
a second, threaded fitting projecting from the housing, the cable extending through the second fitting; and
a nut carried by the second fitting, the nut being in engagement with the generally tubular member closest to the housing such that movement of the nut back and forth on the second fitting causes the generally tubular members to be tightened or loosened.

10. The surgical stabilizer of claim 8, further comprising:
a base leg from which the fingers project; and
a threaded pin that connects the base leg to the first fitting.

11. A surgical stabilizer, comprising:
an elongate handle having a longitudinal axis and distal and proximal ends;
a neck made of a malleable material connected to and extending from the distal end of the handle, the neck having a distal end and a proximal end, the proximal end being connected to the distal end of the handle;
a ball rigidly secured to the proximal end of the neck;
a socket at the distal end of the handle into which the ball can be nested; and
a sleeve disposed about the ball and threaded onto the end of the handle, the sleeve, upon being tightened, compressing the ball into the socket;
a base leg having first and second ends, the base leg being connected to the distal end of the neck;
first and second spaced, generally flat, hollow fingers having a plurality of openings on their underside, the fingers being disposed generally parallel with each other and lying in a plane disposed at an angle from the longitudinal axis of the handle, the first finger having a proximal end connected to the first end of the base leg and the second finger having a proximal end connected to the second end of the base leg; and a hollow tube connected to the fingers, the hollow tube permitting a vacuum to be applied to the fingers.

12. The surgical stabilizer of claim 11, wherein the fingers are made of a malleable material.

13. The surgical stabilizer of claim 11, wherein the neck includes first and second portions that diverge from each other, the first portion being connected to the base leg adjacent the first end thereof, and the second portion being connected to the base leg adjacent the second end thereof.

14. The surgical stabilizer of claim 11, further comprising serrations on the underside of the fingers.

15. The surgical stabilizer of claim 11, wherein the distal ends of the fingers are angled toward each other.

16. The surgical stabilizer of claim 11, wherein the distal ends of the fingers are inclined upwardly from the plane in which the fingers lie.

17. A surgical stabilizer, comprising:

a housing;

a flexible member having a distal end and a proximal end, the proximal end being connected to the housing, the flexible member capable of being tightened into a rigid position when desired, the flexible member including:
 a plurality of generally tubular members disposed in end-to-end relationship;
 a cam disposed within the housing;
 a first fitting disposed at the distal end of the generally tubular members;
 a cable extending through the generally tubular members, the cable being connected at one end to the cam and being connected at the other end to the first fitting, activation of the cam causing the cable to be tightened or loosened;
 a second, threaded fitting projecting from the housing, the cable extending through the second fitting; and
 a nut carried by the second fitting, the nut being in engagement with the generally tubular member closest to the housing such that movement of the nut back and forth on the second fitting causes the generally tubular members to be tightened or loosened;

a pair of spaced, generally flat, hollow fingers having a plurality of openings on their underside, the fingers being connected to the distal end of the flexible member; and a hollow tube connected to the fingers, the hollow tube permitting a vacuum to be applied to the fingers.

18. The surgical stabilizer of claim 17, wherein the housing includes a slot by which the housing can be attached to a mounting bar.

19. The surgical stabilizer of claim 17, further comprising:

a base leg from which the fingers project; and a threaded pin that connects the base leg to the first fitting.

20. The surgical stabilizer of claim 17, further comprising serrations on the underside of the fingers.

* * * * *

UNITED STATES PATENT AND TRADEMARK OFFICE
CERTIFICATE OF CORRECTION

PATENT NO.    : 6,361,492 B1
DATED         : March 26, 2002
INVENTOR(S)   : Santilli, Albert N.

It is certified that error appears in the above-identified patent and that said Letters Patent is hereby corrected as shown below:

Column 10,
Line 11, after "proximal end" insert -- , the proximal end --

Signed and Sealed this

Fourth Day of June, 2002

Attest:

Attesting Officer

JAMES E. ROGAN
Director of the United States Patent and Trademark Office